(12) United States Patent
Yoda et al.

(10) Patent No.: US 6,222,905 B1
(45) Date of Patent: Apr. 24, 2001

(54) IRRADIATION DOSE CALCULATION UNIT, IRRADIATION DOSE CALCULATION METHOD AND RECORDING MEDIUM

(75) Inventors: Kiyoshi Yoda; Nobuyuki Kanematsu, both of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/349,459

(22) Filed: Jul. 9, 1999

(30) Foreign Application Priority Data

Aug. 27, 1998 (JP) .................................................. 10-242184

(51) Int. Cl.$^7$ ...................................................... A61N 5/10
(52) U.S. Cl. ................................................. 378/65; 378/64
(58) Field of Search .......................................... 378/64, 65

(56) References Cited

U.S. PATENT DOCUMENTS

| | | | |
|---|---|---|---|
| 5,291,404 | 3/1994 | Kurokawa et al. | 364/413.26 |
| 5,596,653 | 1/1997 | Kurokawa | 382/128 |
| 5,818,902 | * 10/1998 | Yu | 378/65 |

OTHER PUBLICATIONS

Yoda et al., "Dose Optimization Of Proton And Heavy Ion Therapy Using Generalized Sampled Pattern Matching", Phys. Med. Biol. 42 1997, pp. 2411–2420.

M. Urie, "Treatment Planning For Proton Beams", Ion Beams in Tumor Therapy, 1995, pp. 279–289.

\* cited by examiner

Primary Examiner—David V. Bruce
(74) Attorney, Agent, or Firm—Leydig, Voit & Mayer, Ltd.

(57) ABSTRACT

An irradiation dose calculating unit can solve a problem of a conventional irradiation dose calculating unit in that since irradiation doses from portals are empirically determined, it is likely that optimum irradiation doses are not established for a target and a critical organ. A prescription data input section is used for a physician to input prescription data designating doses to a target and a critical organ. First and second object function calculating sections each calculate predefined indices, and obtain a first object function representing the level of satisfaction for the critical organ and a second object function representing the level of satisfaction for the target and critical organ. The irradiation doses from the portals are calculated based on these object functions such that the prescription data are satisfied.

11 Claims, 12 Drawing Sheets

FIG.7

```
TARGET 82
      MINIMUM DOSE : 58Gy, PRESCRIPTION DOSE : 60Gy,
      MAXIMUM DOSE : 62Gy,
      UNDERDOSE VOLUME FRACTION
      (LESS THAN PRESCRIPTION DOSE) : 5%
CRITICAL ORGAN 84
      LIMITING DOSE : 25Gy
      MAXIMUM DOSE : 20Gy
      OVERDOSE VOLUME FRACTION
      (EQUAL TO OR GREATER THAN MAXIMUM DOSE) : 10%
CRITICAL ORGAN 86
      LIMITING DOSE : 15Gy
      MAXIMUM DOSE : 10Gy
      OVERDOSE VOLUME FRACTION
      (EQUAL TO OR GREATER THAN MAXIMUM DOSE) : 10%
CRITICAL ORGAN 88
      LIMITING DOSE : 15Gy
      MAXIMUM DOSE : 10Gy
      OVERDOSE VOLUME FRACTION
      (EQUAL TO OR GREATER THAN MAXIMUM DOSE) : 10%
CONSTRAINED WEIGHTS :  ALL ONE,
REFERENCE COORDINATES : CENTER OF TARGET 82
```

FIG.8

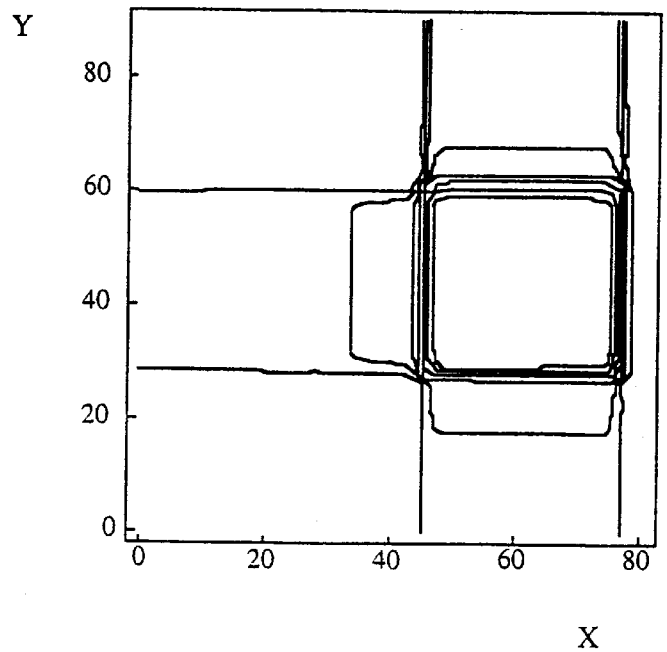

FIG.11

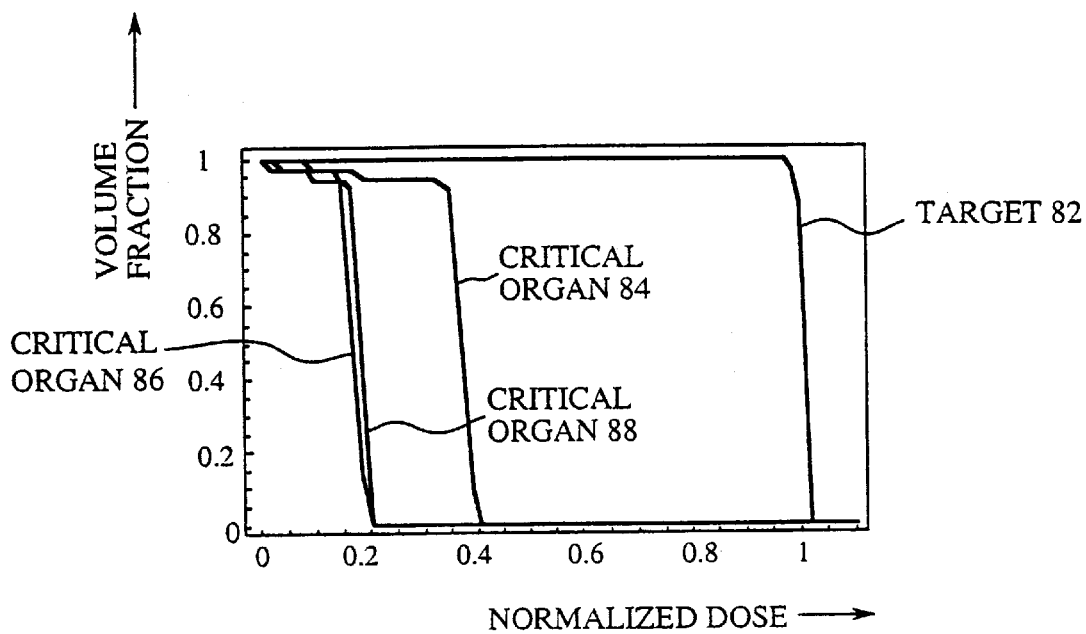

FIG.12

TARGET 82
    MINIMUM DOSE : 58.2Gy, PRESCRIPTION DOSE : 60Gy,
    MAXIMUM DOSE : 60.7Gy,
    UNDERDOSE VOLUME FRACTION
    (LESS THAN PRESCRIPTION DOSE) : 29%
CRITICAL ORGAN 84
    MAXIMUM DOSE : 23.2Gy
    OVERDOSE VOLUME FRACTION
    (EQUAL TO OR GREATER THAN MAXIMUM DOSE
     OF 20 Gy) : 92%
CRITICAL ORGAN 86
    MAXIMUM DOSE : 11.3Gy
    OVERDOSE VOLUME FRACTION
    (EQUAL TO OR GREATER THAN MAXIMUM DOSE
     OF 10 Gy) : 42%
CRITICAL ORGAN 88
    MAXIMUM DOSE : 11.4Gy
    OVERDOSE VOLUME FRACTION
    (EQUAL TO OR GREATER THAN MAXIMUM DOSE
     OF 10 Gy) : 91%

FIG. 13

```
TARGET 82
    MINIMUM DOSE : 58Gy, PRESCRIPTION DOSE : 60Gy,
    MAXIMUM DOSE : 62Gy,
    UNDERDOSE VOLUME FRACTION
    (LESS THAN PRESCRIPTION DOSE) : 5%
CRITICAL ORGAN 84
    LIMITING DOSE : 25Gy
    MAXIMUM DOSE : 25Gy
    OVERDOSE VOLUME FRACTION
    (EQUAL TO OR GREATER THAN MAXIMUM DOSE) : 0%
CRITICAL ORGAN 86
    LIMITING DOSE : 17Gy
    MAXIMUM DOSE : 17Gy
    OVERDOSE VOLUME FRACTION
    (EQUAL TO OR GREATER THAN MAXIMUM DOSE) : 0%
CRITICAL ORGAN 88
    LIMITING DOSE : 9Gy
    MAXIMUM DOSE : 9Gy
    OVERDOSE VOLUME FRACTION
    (EQUAL TO OR GREATER THAN MAXIMUM DOSE) : 0%
CONSTRAINED WEIGHTS : ALL ONE,
REFERENCE COORDINATES : CENTER OF TARGET 82
```

FIG. 14

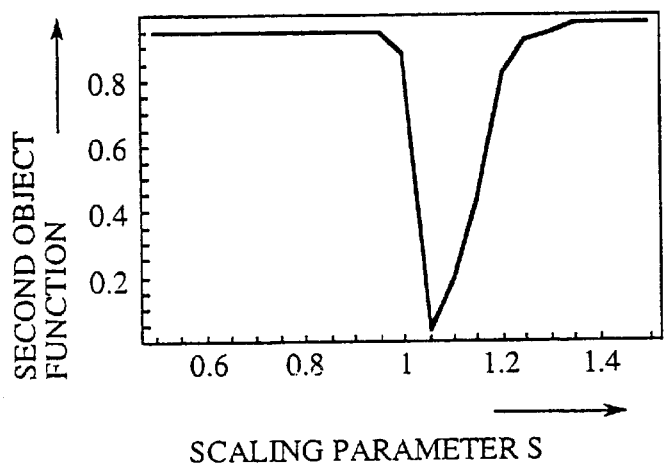

FIG.17

TARGET 82
    MINIMUM DOSE : 58.95Gy, PRESCRIPTION DOSE : 60Gy,
    MAXIMUM DOSE : 61.81Gy,
    UNDERDOSE VOLUME FRACTION
    (LESS THAN PRESCRIPTION DOSE) : 2%
CRITICAL ORGAN 84
    MAXIMUM DOSE : 21.5Gy
    OVERDOSE VOLUME FRACTION
    (EQUAL TO OR GREATER THAN MAXIMUM DOSE
    OF 20 Gy) : 0%
CRITICAL ORGAN 86
    MAXIMUM DOSE : 16.8Gy
    OVERDOSE VOLUME FRACTION
    (EQUAL TO OR GREATER THAN MAXIMUM DOSE
    OF 10 Gy) : 0%
CRITICAL ORGAN 88
    MAXIMUM DOSE : 8.5Gy
    OVERDOSE VOLUME FRACTION
    (EQUAL TO OR GREATER THAN MAXIMUM DOSE
    OF 10 Gy) : 0%

FIG.18

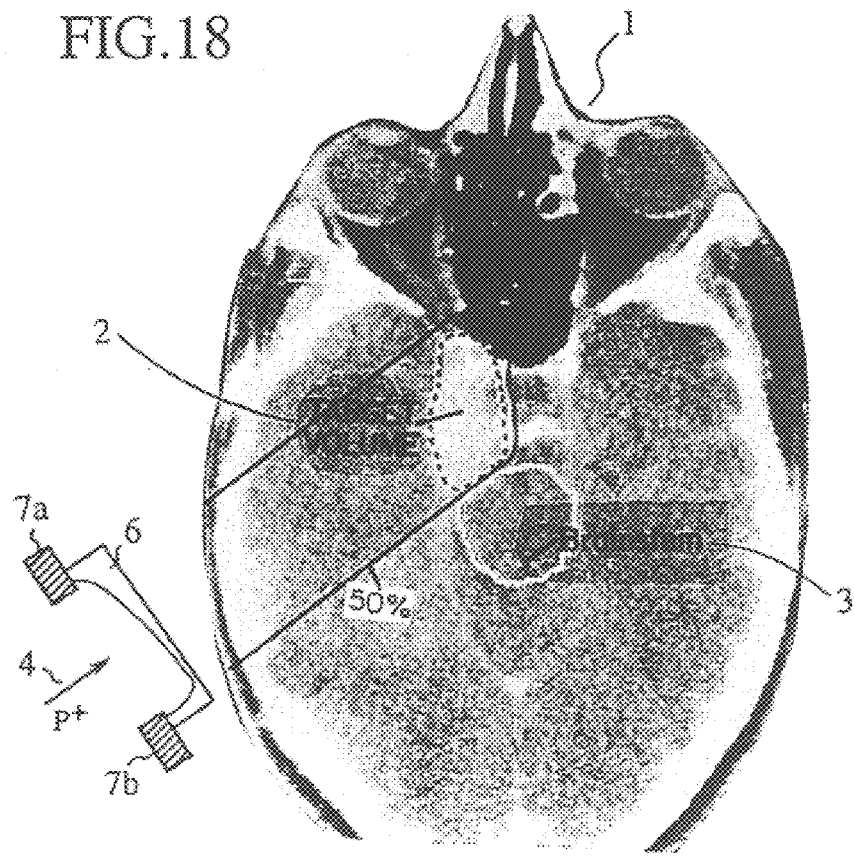

IRRADIATION DOSE CALCULATION UNIT, IRRADIATION DOSE CALCULATION METHOD AND RECORDING MEDIUM

BACKGROUND OF THE INVENTION

1. Field of the Invention

The present invention relates to an irradiation dose calculation unit and an irradiation dose calculation method for calculating from prescription data irradiation doses from one or more portals (directions) to a target, and to a recording medium for recording a program for implementing the irradiation dose calculation method.

2. Description of Related Art

FIG. 18 is a view illustrating proton beam radiation therapy described in M. Urie, "Treatment Planning for Proton Beams", Ion Beams in Tumor Therapy published by CHAPMAN & HALL, pp. 279–289, 1995. In this figure, the reference numeral 1 designates a CT (Computed Tomography) of the head of a subject; 2 designates a target tumor for proton beam radiation; 3 designates a brain stem as a critical organ fragile to radiation; 4 designates a proton beam; 6 designates a bolus for varying the dose distribution in depth direction so as to focus a high dose portion on the location of the tumor 2; and 7a and 7b designate a collimator for matching the lateral beam width to the width of the tumor 2.

To apply the radiation therapy, the target is irradiated by the radiation beam while avoiding critical organs (the brain stem 3, in this case) as shown in FIG. 18. Although the proton bream radiation from a single portal is shown in FIG. 18, radiation from multiple portals (directions) is carried out in actual therapy, and doses from the portals are determined such that normal tissues and critical organs are protected from injury. Since the tolerable doses are known for normal tissues, the doses from the portals are empirically determined such that the doses absorbed by the normal tissues located in radiation paths do not exceed the tolerable doses.

Thus, the conventional irradiation dose calculation method empirically determines the doses from the portals such that the doses absorbed by the normal tissues located in the radiation paths become less than the tolerable doses. This method, however, presents a problem in that optimum doses to the target and critical organs are not always assured.

SUMMARY OF THE INVENTION

The present invention is implemented to solve the foregoing problem. It is therefore an object of the present invention to provide an irradiation dose calculation unit, an irradiation dose calculation method and a recording medium capable of setting appropriate doses in accordance with prescription data by calculating irradiation doses from the portals on the basis of a prescription of the doses for a target and critical organs prescribed by a physician.

According to a first aspect of the present invention, there is provided an irradiation dose calculating unit comprising: a prescription data input section for inputting prescription data which includes a prescription dose, minimum dose, maximum dose and underdose volume fraction for at least one target, and includes a limiting dose, maximum dose and overdose volume fraction for at least one critical organ; an absorbed dose distribution calculating section for calculating body absorbed dose distributions of radiation beams irradiated from a plurality of portals to the target; a first object function calculating means for calculating a first object function from the prescription data, irradiation dose ratios of the radiation beams irradiated from the portals to the target, and the body absorbed dose distributions calculated by the absorbed dose distribution calculating section, the first object function indicating a level of satisfaction of the prescription data for the critical organ; an irradiation dose ratio calculating section for calculating the irradiation dose ratios that optimize the first object function; a second object function calculating section for calculating a second object function from the prescription data and a product of a scaling parameter multiplied by a sum of products which are obtained by multiplying the body absorbed dose distributions for the portals by the irradiated dose ratios of the portals calculated by the irradiation dose ratio calculating section, a second object function indicating a level of satisfaction of the prescription data for the target and the critical organ; a scaling parameter calculating section for calculating the scaling parameter that optimizes the second object function; and an irradiation dose determining section for determining the irradiation doses of the portals from at least the scaling parameter calculated by the scaling parameter calculating section, the irradiation dose ratios of the portals calculated by the irradiation dose radio calculating section, and the body absorbed dose distribution for the portals.

Here, the body absorbed dose distributions may be normalized distributions obtained by dividing the body absorbed dose distributions of the radiation beams irradiated from the portals to the target by an absorbed dose at reference coordinates in the target.

The first object function calculating section may determine one of a first index and a second index as the first object function, the first index being calculated using a maximum value of the absorbed dose distributions in the critical organ, and the second index being calculated using a volume fraction of the critical organ, in which the absorbed dose is equal to or greater than a predetermined absorbed-dose.

The irradiation dose ratio calculating section may determine the irradiation dose ratios of the portals by varying the irradiation dose ratios of the portals step by step from zero to one, by having the first object function calculating section calculate the first object function at each step, and by determining the irradiation dose ratios of the portals when the first object function is optimized.

The irradiation dose ratio calculating section may determine the irradiation dose ratios only for portals whose irradiation dose ratios are yet less than unity.

The irradiation dose ratio calculating section may calculate the irradiation dose ratios using an optimization method selected from a group consisting of an iterative search method, a simulated annealing method, a gradient method, and combinations of at least two of the iterative search method, the simulated annealing method and the gradient method.

The second object function calculating section may determine one of a first index, second index, third index, fourth index and fifth index as the second object function, the first index being calculated using a maximum value in the critical organ of the product of the scaling parameter multiplied by the sum of products which are obtained by multiplying the body absorbed dose distributions for the portals by the irradiated dose ratios of the portals calculated by the irradiation dose ratio calculating section, the second index being calculated using the overdose volume fraction of the critical organ in which the absorbed dose exceeds a predetermined absorbed dose, the third index being calculated using a minimum value in the target of the product of the scaling parameter and the sum of the products, the fourth index being calculated using a maximum value in the target of the product of the scaling parameter and the sum of the products, and the fifth index being calculated using the volume fraction of the target in which the absorbed dose is less than the predetermined absorbed dose.

The irradiation dose determining section may place a product of the scaling parameter and the prescription dose for the target as an absorbed dose at the reference coordinates in the target, and may determine the irradiation doses of the portals from the absorbed dose.

The irradiation dose determining section may place the product of the scaling parameter and the prescription dose for the target as the absorbed dose of the reference coordinates in the target, obtain a proportionality constant by dividing the absorbed dose by the absorbed dose at the reference coordinates obtained from the sum of products of the absorbed dose ratios of the portals and absorbed doses for the portals per unit irradiation dose, and determine the irradiation doses of the portals by multiplying the irradiation dose ratios by the proportionality constant.

According to a second aspect of the present invention, there is provided an irradiation dose calculating method comprising the steps of: inputting prescription data which includes a prescription dose, minimum dose, maximum dose and underdose volume fraction for at least one target, and includes a limiting dose, maximum dose and overdose volume fraction for at least one critical organ; calculating body absorbed dose distributions of radiation beams irradiated from a plurality of portals to the target; calculating a first object function from the prescription data, irradiation dose ratios of the radiation beams irradiated from the portals to the target, and the body absorbed dose distributions, the first object function indicating a level of satisfaction of the prescription data for the critical organ; calculating the irradiation dose ratios that optimize the first object function; calculating a second object function from the prescription data and a product of a scaling parameter multiplied by a sum of products which are obtained by multiplying the body absorbed dose distributions for the portals by the irradiated dose ratios of the portals, a second object function indicating a level of satisfaction of the prescription data for the target and the critical organ; calculating the scaling parameter that optimizes the second object function; and determining the irradiation doses of the portals from at least the scaling parameter calculated, the irradiation dose ratios of the portals calculated, and the body absorbed dose distribution for the portals.

According to a third aspect of the present invention, there is provided a computer usable medium having a computer readable program code means for causing a computer to function as an irradiation dose calculating unit comprising: a prescription data input section for inputting prescription data which includes a prescription dose, minimum dose, maximum dose and underdose volume fraction for at least one target, and includes a limiting dose, maximum dose and overdose volume fraction for at least one critical organ; an absorbed dose distribution calculating section for calculating body absorbed dose distributions of radiation beams irradiated from a plurality of portals to the target; a first object function calculating means for calculating a first object function from the prescription data, irradiation dose ratios of the radiation beams irradiated from the portals to the target, and the body absorbed dose distributions calculated by the absorbed dose distribution calculating section, the first object function indicating a level of satisfaction of the prescription data for the critical organ; an irradiation dose ratio calculating section for calculating the irradiation dose ratios that optimize the first object function; a second object function calculating section for calculating a second object function from the prescription data and a product of a scaling parameter multiplied by a sum of products which are obtained by multiplying the body absorbed dose distributions for the portals by the irradiated dose ratios of the portals calculated by the irradiation dose ratio calculating section, a second object function indicating a level of satisfaction of the prescription data for the target and the critical organ; a scaling parameter calculating section for calculating the scaling parameter that optimizes the second object function; and an irradiation dose determining section for determining the irradiation doses of the portals from at least the scaling parameter calculated by the scaling parameter calculating section, the irradiation dose ratios of the portals calculated by the irradiation dose radio calculating section, and the body absorbed dose distribution for the portals.

BRIEF DESCRIPTION OF THE DRAWINGS

FIG. 7 is an example of prescription data for the human body model of FIG. 6;

FIG. 8 is an isocontour plot illustrating an example of a dose distribution in the human body model;

FIG. 11 is a graph illustrating an example of relationships between a normalized dose and volume fractions of a target and critical organs;

FIG. 12 is an example of an underdose volume fraction of the target, overdose volume fractions of critical organs and the like;

FIG. 13 is another example of prescription data for the human body model of FIG. 6;

FIG. 14 is a graph illustrating another example of relationships between the scaling parameter and the second object function;

FIG. 17 is another example of the underdose volume fraction of the target, the overdose volume fractions of the critical organs and the like; and FIG. 18 is a view illustrating a proton beam radiation therapy.

DETAILED DESCRIPTION OF THE PREFERRED EMBODIMENTS

The invention will now be described with reference to the accompanying drawings.

EMBODIMENT 1

Figure 1:
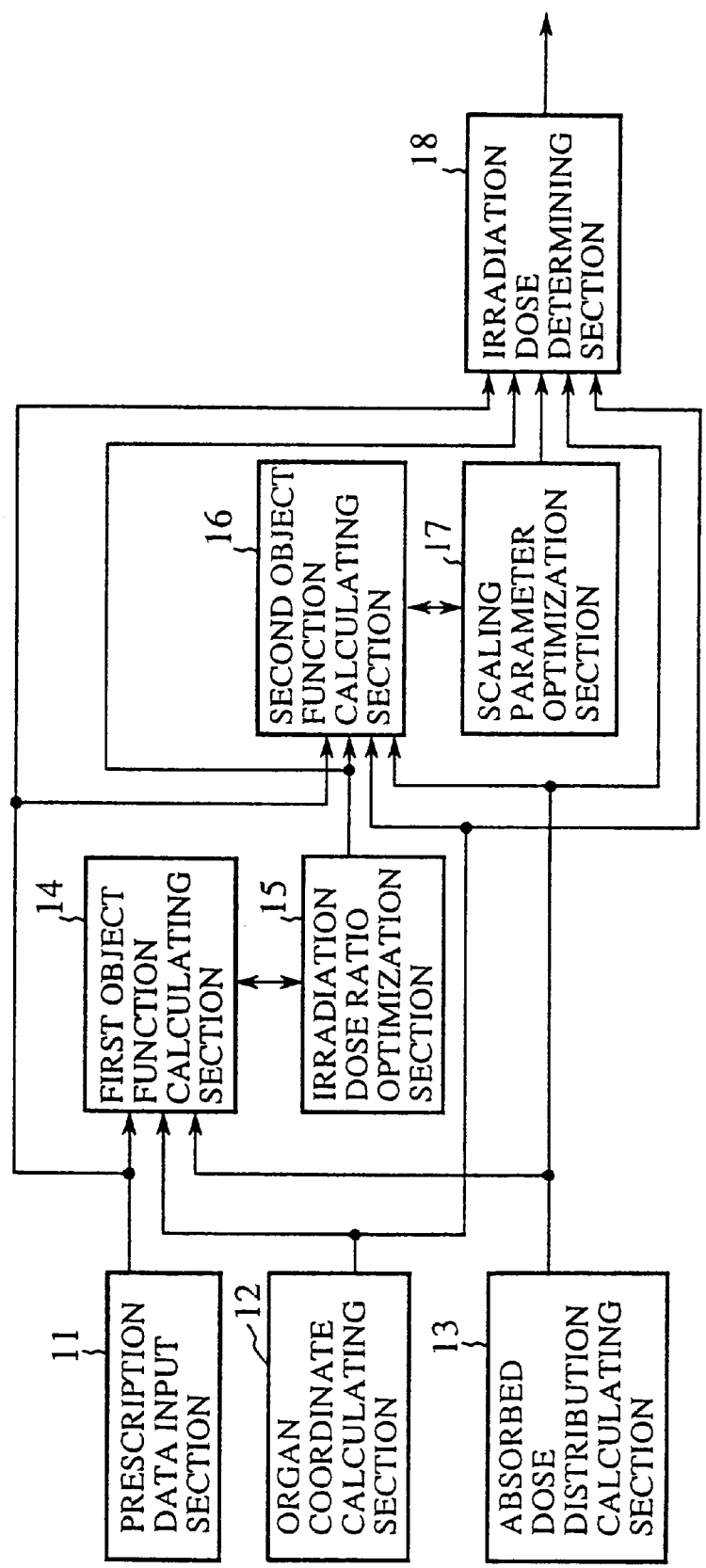
FIG. 1 is a block diagram showing an embodiment 1 of an irradiation dose calculation unit in accordance with the present invention.

FIG. 1 is a block diagram showing an embodiment 1 of an irradiation dose calculation unit in accordance with the present invention. In FIG. 1, the reference numeral 11 designates a prescription data input section for a physician to input prescription data. The prescription data includes reference coordinates, a prescription dose, a maximum dose, a minimum dose, and an underdose volume fraction of each target; a limiting dose, a maximum dose and an overdose volume fraction of each critical organ; and constraint weights indicative of the importance of individual targets and critical organs. Here, the underdose volume fraction is the upper limit of the volume fraction of the target that is exposed to irradiation less than the minimum dose, and the overdose volume fraction is the upper limit of the volume fraction of the critical organ that is exposed to irradiation greater than the maximum dose. The reference numeral 12 designates an organ coordinate calculating section for calculating from image data the coordinates or range of the targets and critical organs designated on the image data such as CT data. The reference numeral 13 designates an absorbed dose distribution calculating section for calculating absorbed dose distribution for individual portals when a unit dose is radiated from the portals on the basis of the image data such as the CT data and data indicative of human body structure between the targets and irradiation locations.

The reference numeral 14 designates a first object function calculating section for calculating a first object function indicating the level of satisfaction of the prescription data about the critical organs. The first object function is calculated on the basis of the prescription data, coordinates of the targets and critical organs, absorbed dose distribution, and irradiation dose ratios of radiation beams from the portals to the targets. The irradiation dose ratios are supplied from an irradiation dose ratio optimization section 15.

The reference numeral 15 designates the irradiation dose ratio optimization section for supplying the first object function calculating section 14 with the dose ratios of the radiation beams from the portals to the targets, and for supplying a second object function calculating section 16 with irradiation dose ratios when the first object function satisfies a predetermined condition. The irradiation dose ratio optimization section 15 obtains the dose ratios to be supplied to the second object function calculating section 16 by receiving from the first object function calculating section 14 the first object function corresponding to the dose ratios supplied to the first object function calculating section 14, and by successively varying the dose ratios supplied to the first object function calculating section 14 until the first object function satisfies the predetermined condition.

The reference numeral 16 designates the second object function calculating section for calculating a second object function indicating the level of satisfaction of the prescription data about the targets and critical organs. The second object function is calculated on the basis of the prescription data, coordinates of the targets and critical organs, absorbed dose distribution, dose ratios of the radiation beams from the portals to the target, and a scaling parameter. The dose ratios are supplied from the irradiation dose ratio optimization section 15, and the scaling parameter is supplied from a scaling parameter optimization section 17.

The reference numeral 17 designates the scaling parameter optimization section for supplying the second object function calculating section 16 with the scaling parameter by which the absorbed dose distribution is multiplied, and for supplying an irradiation dose determining section 18 with the scaling parameter when the second object function satisfies a predetermined condition. The scaling parameter optimization section 17 obtains the scaling parameter to be supplied to the irradiation dose determining section 18 by receiving from the second object function calculating section 16 the second object function corresponding to the scaling parameter supplied to the second object function calculating section 16, and by successively varying the scaling parameter supplied to the second object function calculating section 16 until the second object function satisfies the predetermined condition.

Figure 5:
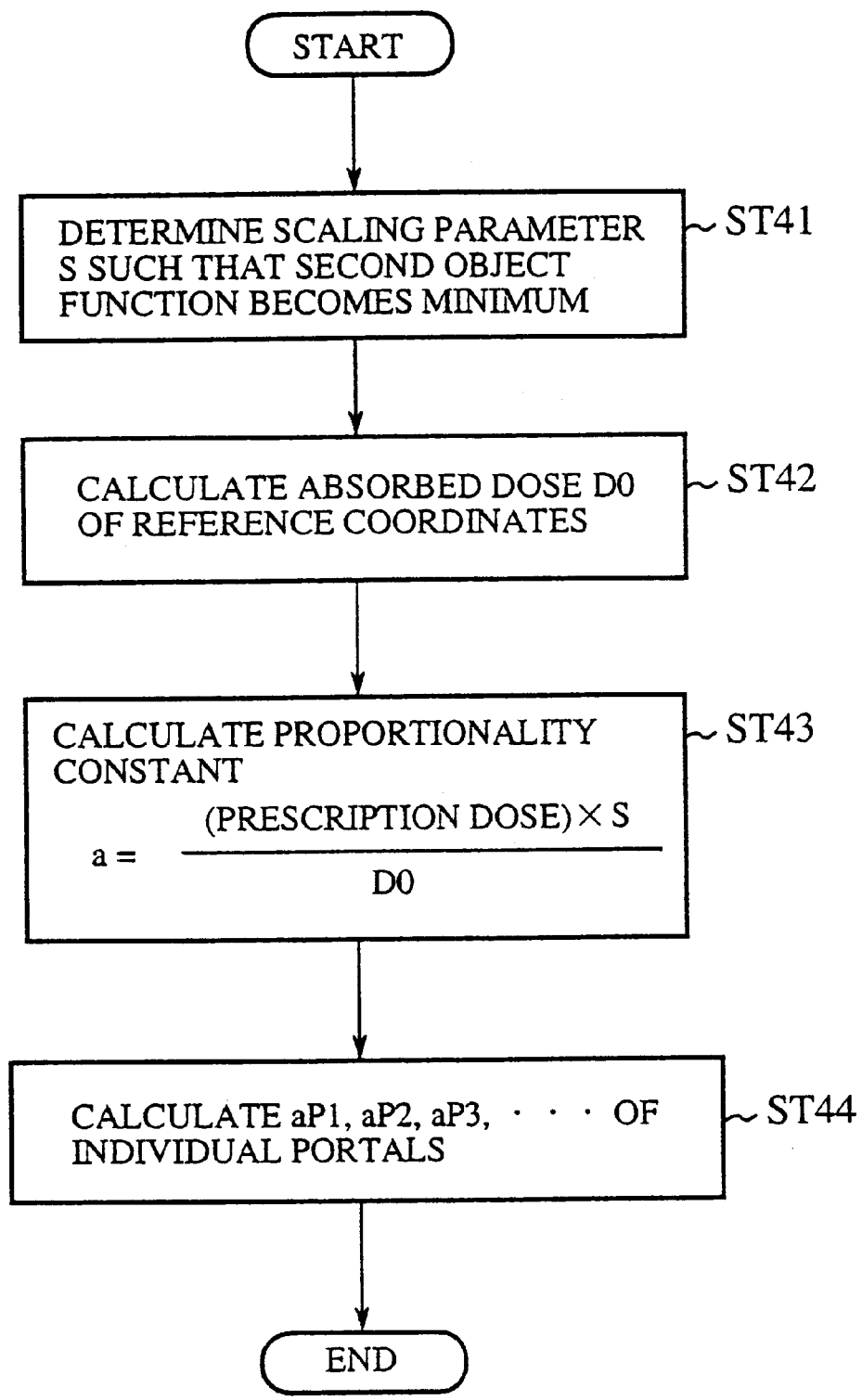
FIG. 5 is a flowchart illustrating an operation of a scaling parameter optimization section and an irradiation dose determining section.

The reference numeral 18 designates the irradiation dose determining section for determining the irradiation dose from the individual portals by multiplying the irradiation dose ratios of the portals by a proportionality constant that is obtained at step ST43 of FIG. 5, which will be described later.

Next, the operation of the present embodiment 1 will be described.

Figure 2:
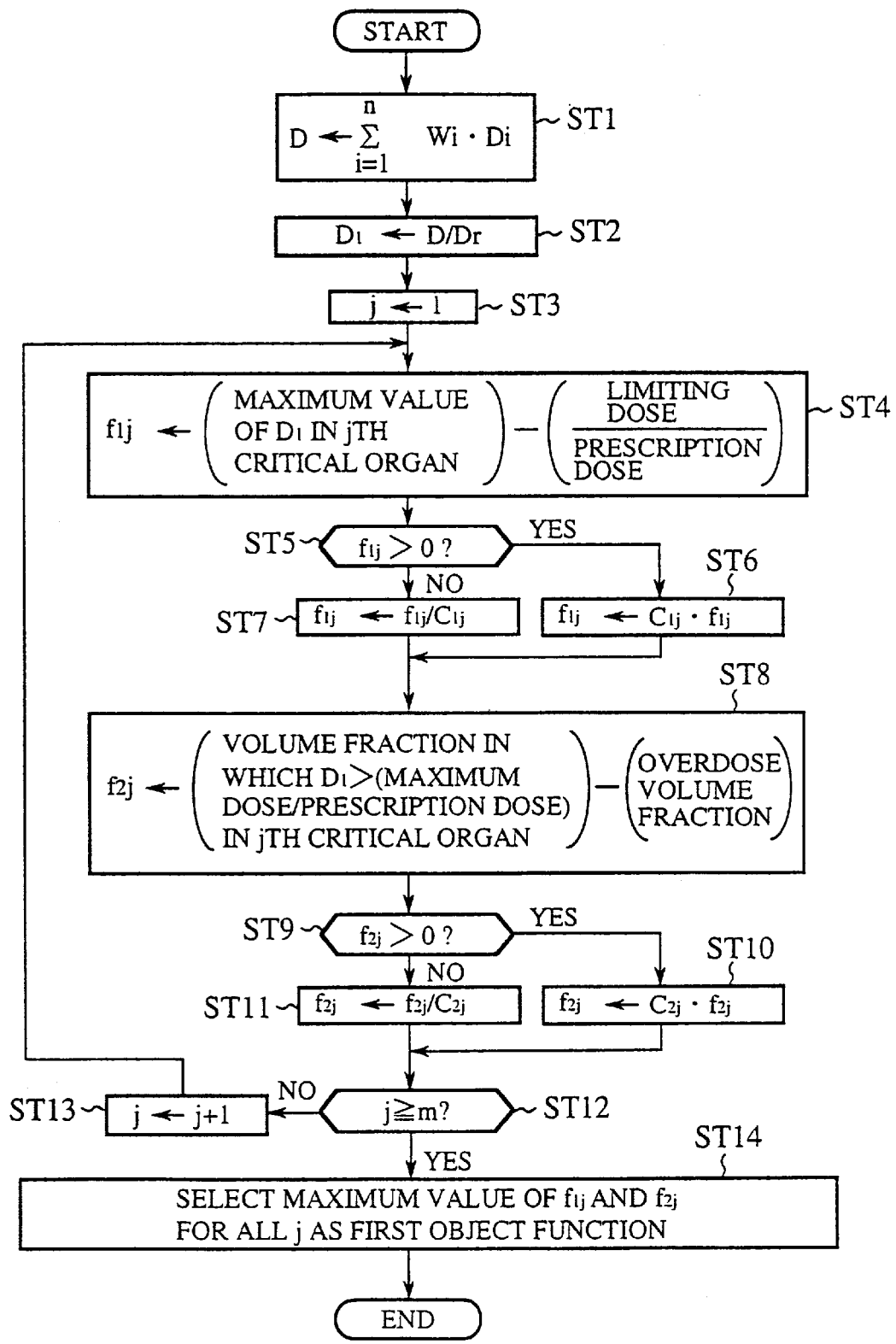
FIG. 2 is a flowchart illustrating an operation of a first object function calculating section.
Figure 3:
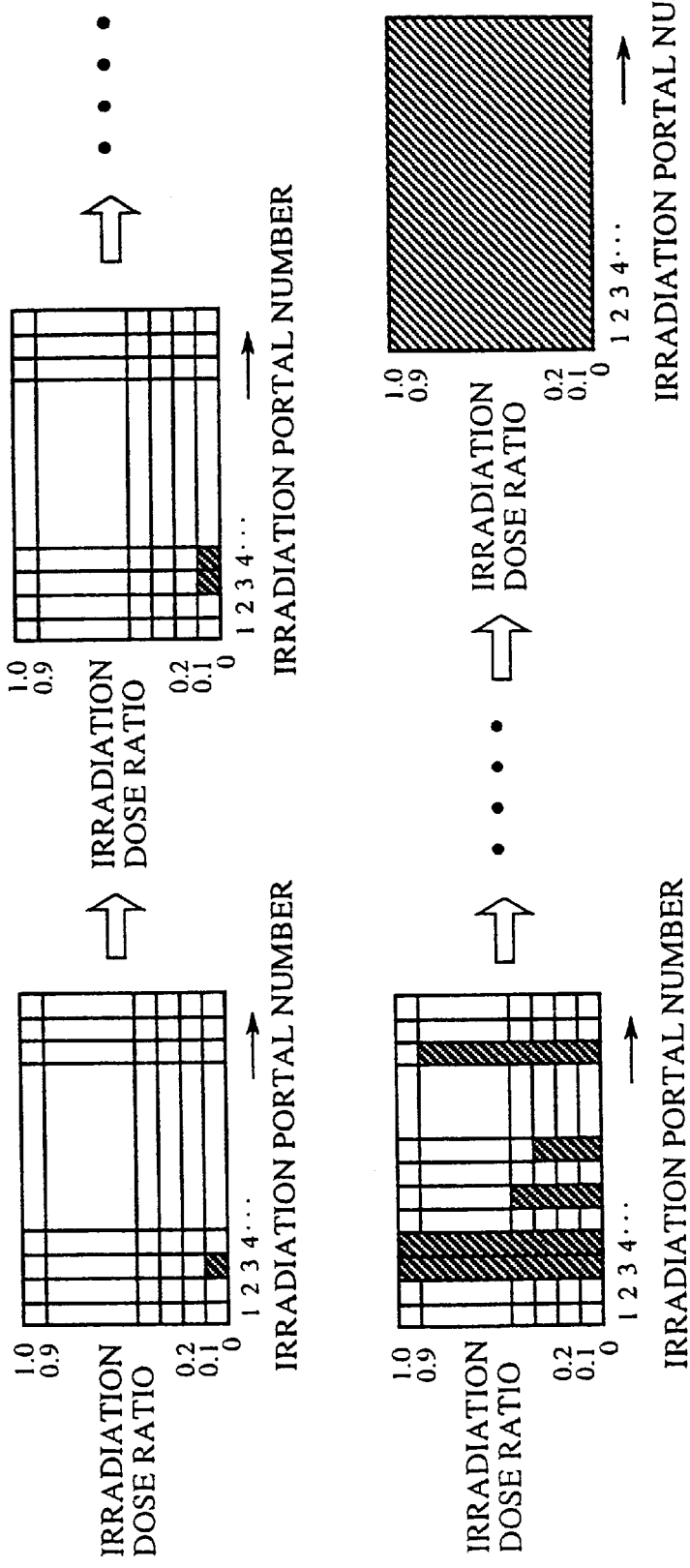
FIG. 3 is a diagram illustrating an operation of an irradiation dose ratio optimization section.
Figure 4:
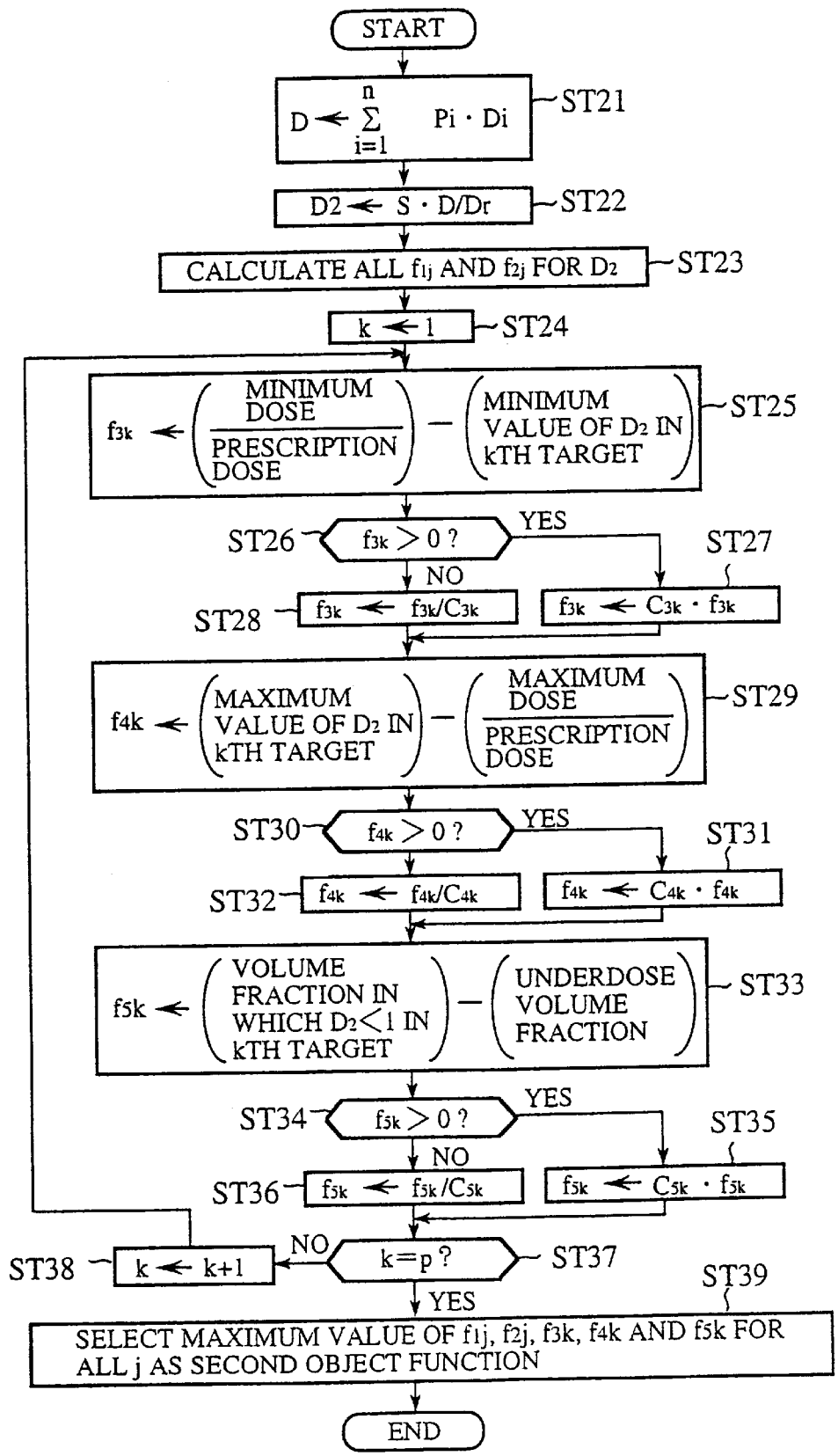
FIG. 4 is a flowchart illustrating an operation of a second object function calculating section.

FIG. 2 is a flowchart illustrating the operation of the first object function calculating section 14. FIG. 3 is a diagram illustrating the operation of the irradiation dose ratio optimization section 15. FIG. 4 is a flowchart illustrating the operation of the second object function calculating section 16. FIG. 5 is a flowchart illustrating the operation of the scaling parameter optimization section 17 and irradiation dose determining section 18.

First, the prescription data are input through the prescription data input section 11. The prescription data include the reference coordinates in each target (a reference point in the target, the center of the target, for example), the prescription dose (an absorbed dose of 60 grays is a standard for cancer), maximum dose, minimum dose, underdose volume fraction of the target; the limiting dose, maximum dose, overdose volume fraction of each critical organ; and constrained weights indicative of importance (degree of caution) of the individual critical organs. The greater constrained weight indicates that the more care must be taken of the critical organ. The input prescription data are supplied to the first object function calculating section 14, second object function calculating section 16 and irradiation dose determining section 18.

The organ coordinate calculating section 12 reads from a recording medium (not shown) image data such as CT data of the designated targets and critical organs, and calculates from the image data the coordinates of the targets and critical organs, that is, their ranges on the image data. The coordinates of the targets and critical organs calculated are supplied to the first object function calculating section 14, second object function calculating section 16 and irradiation dose determining section 18. Sometimes, a physician manually extracts the coordinates.

The absorbed dose distribution calculating section 13 reads from the recording medium the image data such as the CT data and data representing the human body structure between the targets and the radiation positions, and calculates, from these data, body absorbed dose distributions per unit irradiation dose from the individual portals. The body absorbed dose distributions calculated are supplied to the first object function calculating section 14, second object function calculating section 16 and irradiation dose determining section 18.

Subsequently, the first object function calculating section 14 calculates the first object function of the prescription data for the critical organs. The first object function is calculated from the prescription data, coordinates of the targets and critical organs, the body absorbed dose distributions, and the dose ratios of the radiation beams from the portals to the targets which are supplied from the irradiation dose ratio optimization section 15. The operation of the first object function calculating section 14 will now be described in more detail with reference to the flowchart of FIG. 2.

Here, the first object function represents the level of satisfaction of the prescription data for the critical organs. Taking a value in a range from −1 to +1, a decreasing value of the first object function represents an increasing level of satisfaction. This holds true for the following first and second indices.

At step ST1, the first object function calculating section 14 calculates the total absorbed dose distribution D over all n portals by obtaining the sum of products of $W_i$ and $D_i$, where i designates the portal number, $W_i$ denotes the dose ratio of the radiation beam from the portal i to the targets, and $D_i$ denotes the body absorbed dose distribution for the portal i.

Subsequently, at step ST2, the first object function calculating section 14 calculates a normalized absorbed dose distribution $D_1$ by normalizing the total absorbed dose distribution D by the total absorbed dose $D_r$ at the reference coordinates such as at the center of one of the targets.

At step ST3, the count value of a counter j for counting the number of the critical organs is set to one.

At step ST4, the first object function calculating section 14 calculates, from the coordinates of the critical organs and the normalized absorbed dose distribution $D_1$, the maximum value of the normalized absorbed dose distribution $D_1$ in the jth critical organ, and subtracts from the maximum value the quotient obtained by dividing the limiting dose of the jth critical organ by the prescription dose for the target, thereby calculating the first index $f_{1j}$ for the jth critical organ.

At step ST5, the first object function calculating section 14 decides on whether the first index $f_{1j}$ is positive or not. If it is positive, the first object function calculating section 14 changes at step ST6 the first index $f_{1j}$ to a product obtained by multiplying the first index $f_{1j}$ by the constrained weight $C_{1j}$ of the jth critical organ. In contrast, if it is negative, the first object function calculating section 14 changes at step ST7 the first index $f_{1j}$ to a quotient obtained by dividing the first index $f_{1j}$ by the constrained weight $C_{1j}$ of the jth critical organ.

Here, the constrained weights $C_{1j}$, which are set greater than zero and equal to or less than a predetermined value (10, for example), are factors for determining the relative importance of the indices, with representing higher importance as they increase. On the other hand, the indices each take a negative value when the prescription data are satisfied, and a positive value when the prescription data are not satisfied. Thus, the reason for dividing the indices by the constrained weights when they are negative and multiplying the indices by the constrained weights when they are positive is to increase the values of the indices for greater constrained weights, and to indicate that the level of satisfaction of the prescription data decreases as the values of the indices increase.

Subsequently, at step ST8, the first object function calculating section 14 calculates the volume fraction of the jth critical organ. The volume fraction is calculated from the maximum dose for the critical organ and the prescription dose for the target which are included in the prescription data, coordinates of the critical organ, and the normalized absorbed dose distribution $D_1$. Here, the volume fraction is defined as a fraction of the volume of the critical organ, in which the normalized absorbed dose distribution $D_1$ is greater than the quotient obtained by dividing the maximum dose by the prescription dose. Then, the first object function calculating section 14 subtracts from the volume fraction the overdose volume fraction, thereby calculating a second index $f_{2j}$ of the jth critical organ.

At step ST9, the first object function calculating section 14 decides on whether the second index $f_{2j}$ is positive or not. If it is positive, the first object function calculating section 14 changes at step ST10 the second index $f_{2j}$ to a product obtained by multiplying the second index $f_{2j}$ by the constrained weight $C_{2j}$ of the jth critical organ. In contrast, if it is negative, the first object function calculating section 14 changes at step ST11 the second index $f_{2j}$ to a quotient obtained by dividing the second index $f_{2j}$ by the constrained weight $C_{2j}$ of the jth critical organ. The constrained weight $C_{2j}$ is greater than zero and is equal to or less than a predetermined value (10, for example).

At step ST12, the first object function calculating section 14 makes a decision as to whether the counter number j is equal to or greater than the total number m of the critical organs. If j is less than m, the first object function calculating section 14 increments the counter number j by one at step ST13, and returns to step ST4 to calculate the next first index, and then the next second index of the critical organ.

On the other hand, if j is equal to or greater than m, that is, if the first and second indices of all the critical organs are calculated, the first object function calculating section 14 determines at step ST14 the maximum one of the first and second indices of all the critical organs as the first object function. This means that the worst index of the first and second indices is selected as the first object function.

The first object function obtained in this way by the first object function calculating section 14 is supplied to the irradiation dose ratio optimization section 15. Incidentally, the second index calculation (steps ST8–ST11) can precede the first index calculation (steps ST4–ST7), or they can be carried out in parallel. Alternatively, the calculations as shown in FIG. 2 can be replaced by other calculations which are mathematically equivalent.

Next, the irradiation dose ratio optimization section 15, receiving from the first object function calculating section 14 the first object function corresponding to the irradiation dose ratios, successively varies the irradiation dose ratios to be supplied to the first object function calculating section 14 as illustrated in FIG. 3 until the first object function becomes minimum, that is, becomes best, and supplies the second object function calculating section 16 with the irradiation dose ratios when the first object function becomes minimum.

More specifically, the irradiation dose ratio optimization section 15 varies the irradiation dose ratios of the portals from zero to one step by step (by an increment of 0.1, for example), and iteratively searches the irradiation dose ratios at which the first object function satisfies a predetermined condition. In this case, the irradiation dose ratio optimization section 15 can determine the irradiation dose ratios of the portals by having the first object function calculating section 14 calculate the first object function at each step only with the portals whose irradiation dose ratios are less than one, and by picking up the dose ratios of these portals when the first object function satisfies the predetermined condition. In the actual search, the irradiation dose ratios of the portals are increased step by step such that the first object function is always reduced.

Subsequently, the second object function calculating section 16 calculates the second object function about the prescription data for the targets and critical organs. The second object function is calculated from the prescription data, coordinates of the targets and critical organs, the body absorbed dose distributions, the dose ratios of the radiation beams from the portals to the target which are supplied from the irradiation dose ratio optimization section 15, and the scaling parameter supplied from the scaling parameter optimization section 17. The operation of the second object function calculating section 16 will now be described in more detail with reference to the flowchart of FIG. 4.

Here, the second object function represents the level of satisfaction of the prescription data for the targets and critical organs. Taking a value in a range from −1 to +1, a decreasing value of the second object function indicates an increasing level of satisfaction. This holds true for the following first to fifth indices.

At step ST21, the second object function calculating section 16 calculates the total absorbed dose distribution D over all n portals by obtaining the sum of products of $P_i$ and $D_i$, where i designates the portal number, $P_i$ denotes the dose ratio of the radiation beam from the portal i to the target, and $D_i$ denotes the body absorbed dose distribution for the portal i.

Subsequently, at step ST22, the second object function calculating section 16 calculates a normalized absorbed dose distribution $D_2$ by normalizing the product of the total absorbed dose distribution D and the scaling parameter S by the total absorbed dose $D_r$ at the reference coordinates such as at the center of one of the targets.

At step ST23, the second object function calculating section 16 carries out the steps ST4-ST13 of FIG. 2 to calculate the first and second indices $f_{1j}$ and $f_{2j}$ of the individual critical organs j. In this case, the normalized absorbed dose distribution $D_2$ is used in place of the normalized absorbed dose distribution $D_i$.

At step ST24, the count value of a counter k for counting the number of the targets is set to one.

At step ST25, the second object function calculating section 16 calculates, from the coordinates of the target and the normalized absorbed dose distribution $D_2$, the minimum value of the normalized absorbed dose distribution $D_2$ in the kth target, and subtracts the minimum value from the quotient obtained by dividing the minimum dose of the kth target, which is included in the prescription data, by the prescription dose for the target, thereby calculating the third index $f_{3k}$ for the kth target.

At step ST26, the second object function calculating section 16 decides on whether the third index $f_{3k}$ is positive or not. If it is positive, the second object function calculating section 16 changes at step ST27 the third index $f_{3k}$ to a product obtained by multiplying the third index $f_{3k}$ by the constrained weight $C_{3k}$ of the kth target. In contrast, if it is negative, the second object function calculating section 16 changes at step ST28 the third index $f_{3k}$ to a quotient obtained by dividing the third index $f_{3k}$ by the constrained weight $C_{3k}$ of the kth target. The reason for carrying out such changes is the same as that of the first index described above. The constrained weight $C_{3k}$ is greater than zero and is equal to or less than a predetermined value (10, for example).

At step ST29, the second object function calculating section 16 calculates, from the coordinates of the target and the normalized absorbed dose distribution $D_2$, the maximum value of the normalized absorbed dose distribution $D_2$ in the kth target, and subtracts from the maximum value the quotient obtained by dividing the maximum dose of the kth target, which is included in the prescription data, by the prescription dose for the target, thereby calculating the fourth index f4k for the kth target.

At step ST30, the second object function calculating section 16 decides on whether the fourth index $f_{4k}$ is positive or not. If it is positive, the second object function calculating section 16 changes at step ST31 the fourth index $f_{4k}$ to a product obtained by multiplying the fourth index $f_{4k}$ by the constrained weight $C_{4k}$ of the kth target. In contrast, if it is negative, the second object function calculating section 16 changes at step ST32 the fourth index $f_{4k}$ to a quotient obtained by dividing the fourth index $f_{4k}$ by the constrained weight $C_{4k}$ of the kth target. The constrained weight $C_{4k}$ is greater than zero and is equal to or less than a predetermined value (10, for example).

Subsequently, at step ST33, the second object function calculating section 16 calculates the volume fraction of the kth target from the coordinates of the target and the normalized absorbed dose distribution $D_2$, where the volume fraction is defined as a fraction of the volume, in which the normalized absorbed dose distribution $D_2$ is less than one. Then, the second object function calculating section 16 subtracts from the volume fraction the underdose volume fraction, thereby calculating a fifth index $f_{5k}$ of the kth target.

At step ST34, the second object function calculating section 16 decides on whether the fifth index $f_{5k}$ is positive or not. If it is positive, the second object function calculating section 16 changes at step ST35 the fifth index $f_{5k}$ to a product obtained by multiplying the fifth index $f_{5k}$ by the constrained weight $C_{5k}$ of the kth target. In contrast, if it is negative, the second object function calculating section 16 changes at step ST36 the fifth index $f_{5k}$ to a quotient obtained by dividing the fifth index $f_{5k}$ by the constrained weight $C_{5k}$ of the kth target. The constrained weight $C_{5k}$ is greater than zero and is equal to or less than a predetermined value (10, for example).

At step ST37, the second object function calculating section 16 makes a decision as to whether the counter number k is equal to or greater than the total number p of the targets. If k is less than p, the second object function calculating section 16 increments the counter number k by one at step ST38, and returns to step ST25 to calculate the third to fifth indices of the next target.

On the other hand, if k is equal to or greater than p, that is, if the third to fifth indices of all the targets are calculated, the second object function calculating section 16 determines at step ST39 the maximum value of the first and second indices of all the critical organs and of the third to fifth indices of all the targets as the second object function.

The second object function obtained in this way by the second object function calculating section 16 is supplied to the scaling parameter optimization section 17. Incidentally, the third index calculation (steps ST25–ST28), the fourth index calculation (steps ST29–ST32) and the fifth index calculation (steps ST33–ST36) can be carried out in any desired sequence, or in parallel. Likewise the first and second index calculations at step ST23 can be carried out in parallel. Furthermore, the calculations as shown in FIG. 4 can be replaced by another calculation method which is mathematically equivalent.

Next, the scaling parameter optimization section 17, receiving from the second object function calculating section 16 the second object function corresponding to the scaling parameter supplied to the second object function calculating section 16, successively varies the scaling parameter to be supplied to the second object function calculating section 16 until the second object function becomes minimum, that is becomes optimum, and supplies the irradiation dose determining section 18 with the scaling parameter when the second object function satisfies the predetermined condition as the optimum scaling factor. The irradiation dose determining section 18 determines the irradiation doses of the individual portals by multiplying the irradiation dose ratios of the portals by the proportionality constant obtained at step ST43 of FIG. 5. The operation of the scaling parameter optimization section 17 and irradiation dose determining section 18 will now be described in detail with reference to the flowchart of FIG. 5.

First, at step ST41, the scaling parameter optimization section 17 calculates the optimum scaling parameter as described above, and supplies it to the irradiation dose determining section 18.

Subsequently, at step ST42, the irradiation dose determining section 18 calculates the absorbed dose D0 at the reference coordinates from the body absorbed dose distribution (that is, $\Sigma P_i D_i$ at step ST21) obtained as the sum of products of the irradiation dose ratios of the portals and the absorbed doses for the portals per unit irradiation dose; calculates at step ST43 the proportionality constant a by dividing the product of the prescribed dose for the target and the scaling parameter by the absorbed dose D0; and determines the irradiation doses of the portals $aP_i$, $aP_2$, . . . , $aP_n$ by multiplying the irradiation dose ratios $P_1$, $P_2$, . . . , $P_n$ by the proportionality constant a.

Thus, the irradiation doses of the portals are determined.

Next, taking a more concrete example, processing of determining the irradiation doses of the portals will be described.

Figure 6:
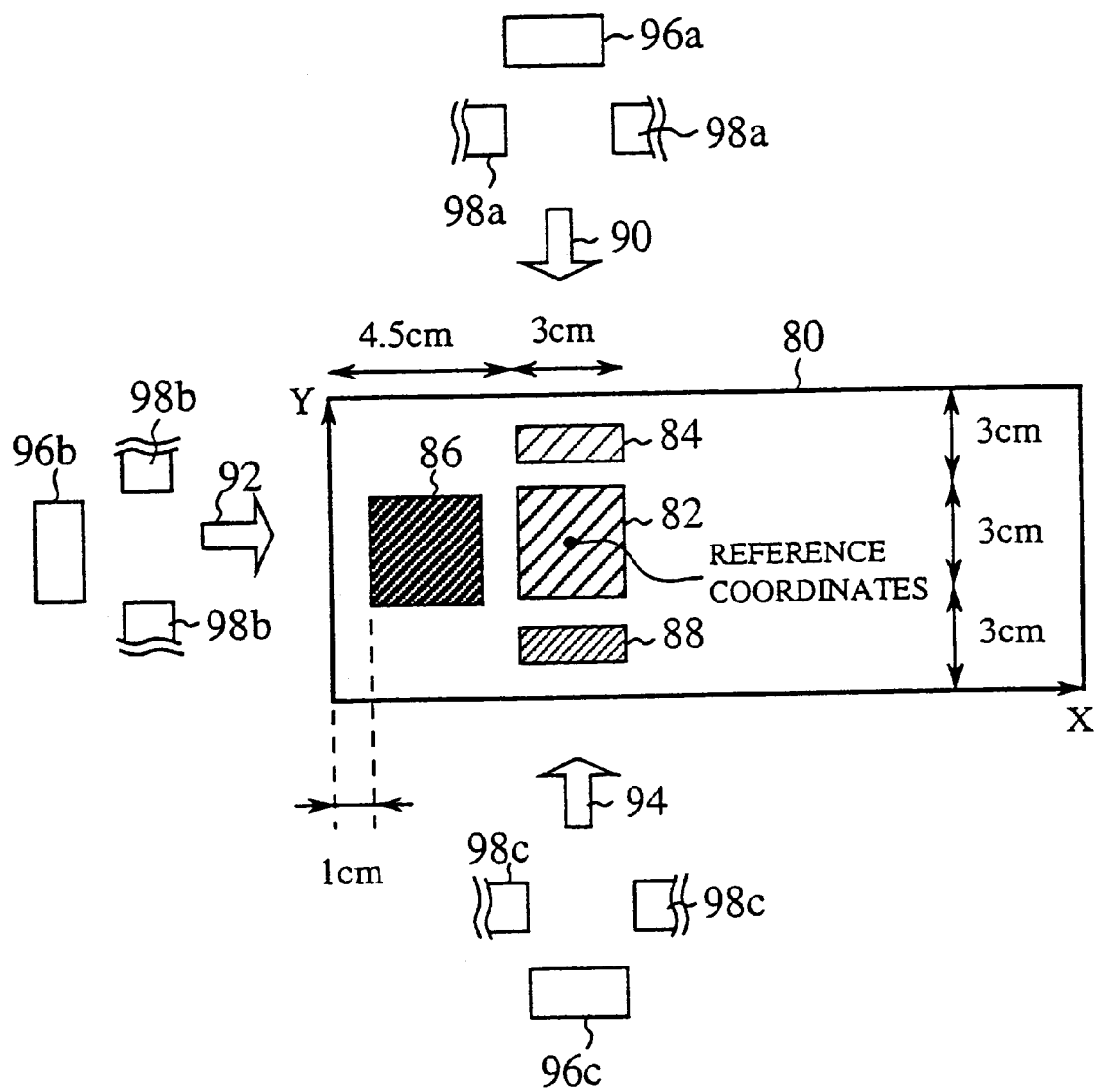
FIG. 6 is a diagram illustrating a human body model having a target irradiated by proton beams from three portals.
Figure 9:
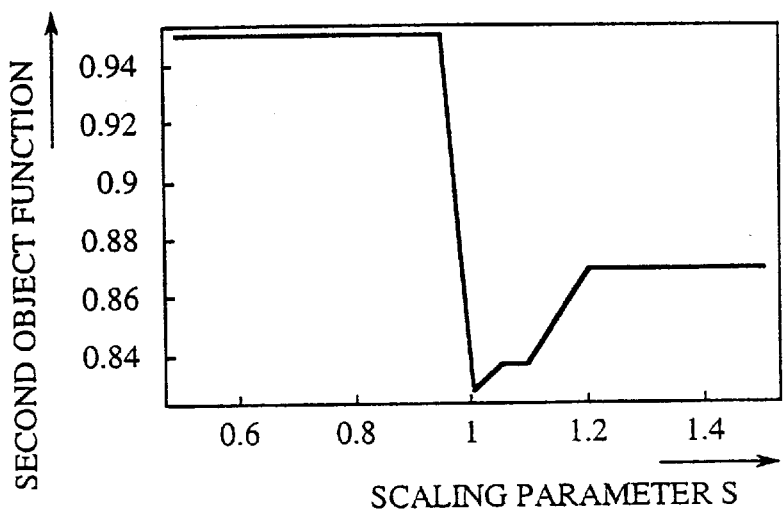
FIG. 9 is a graph illustrating an example of relationships between a scaling parameter and a second object function.
Figure 10:
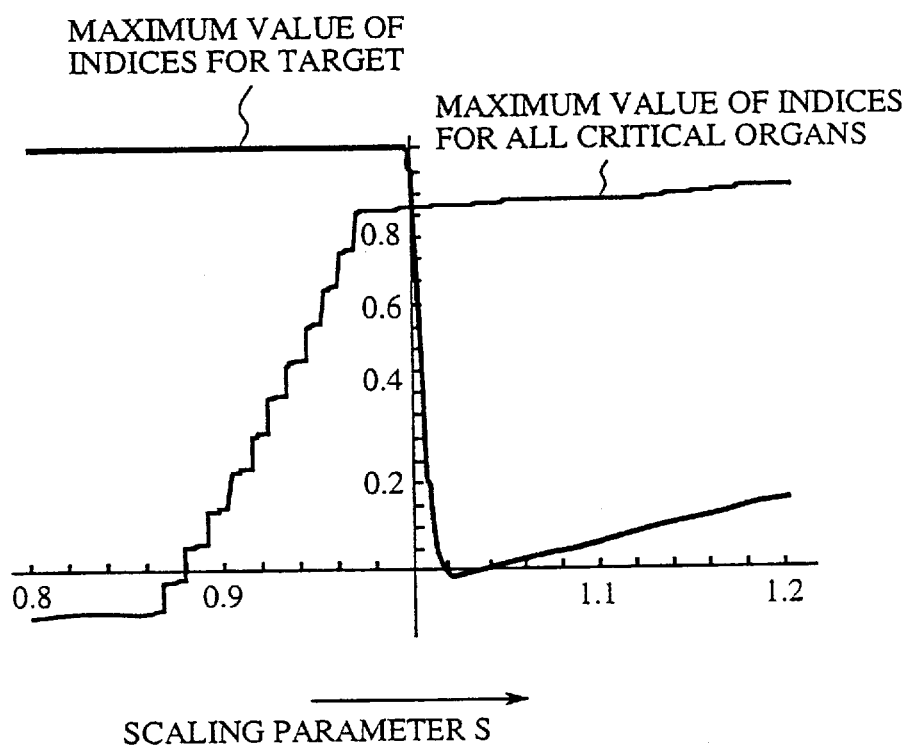
FIG. 10 is a graph illustrating an example of relationships of the scaling parameter with the maximum value of first and second indices and with the maximum value of third to fifth indices when determining and the second object function.

FIG. 6 is a diagram illustrating a human body model having a target irradiated by proton beams from three portals. FIG. 7 is an example of prescription data for the human body model of FIG. 6. FIG. 8 is an isocontour plot illustrating an example of a dose distribution in the human body model. FIG. 9 is a graph illustrating an example of relationships between the scaling parameter and the second object function. FIG. 10 is a graph illustrating an example of relationships of the scaling parameter with the maximum value of the first and second indices and with the maximum value of the third to fifth indices when determining the second object function. FIG. 11 is a graph illustrating an example of relationships between the normalized dose and the volume fractions of the target and critical organs. FIG. 12 is an example of underdose volume fraction of the target, overdose volume fractions of the critical organs and so on.

Figure 15:
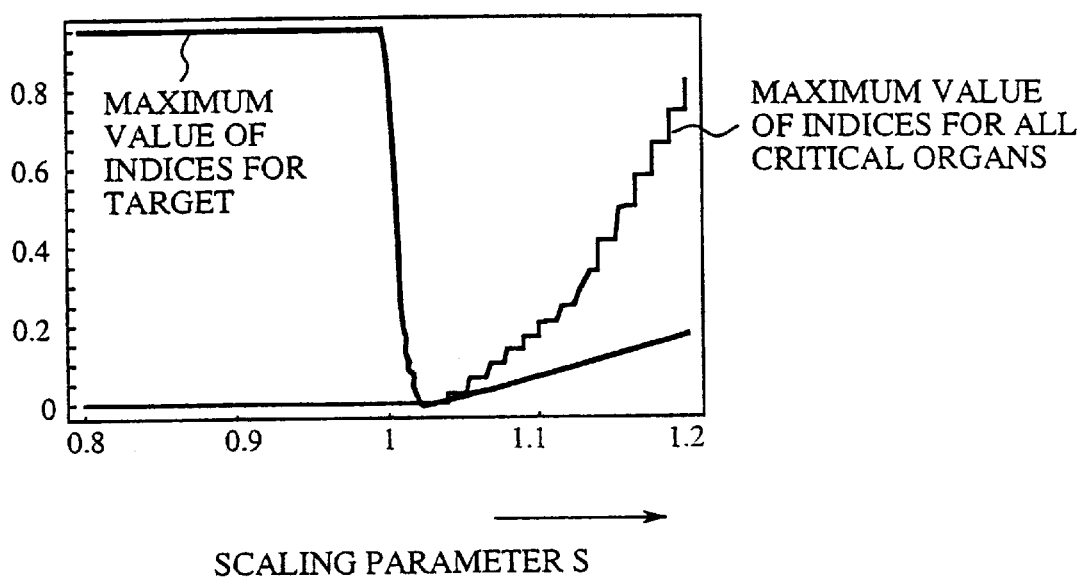
FIG. 15 is a graph illustrating another example of relationships of the scaling parameter with the maximum value of the first and second indices and with the maximum value of the third to fifth indices when determining the second object function.
Figure 16:
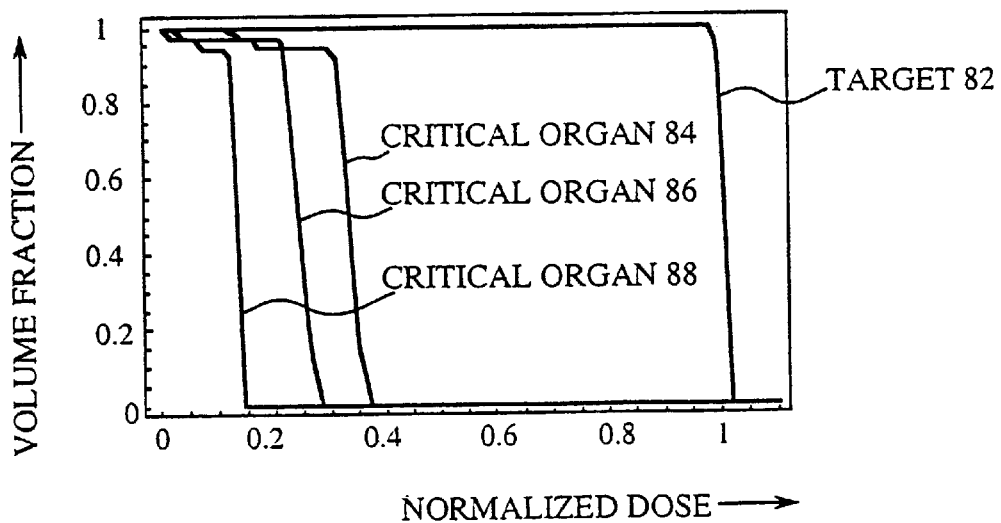
FIG. 16 is a graph illustrating another example of relationships between the normalized dose and the volume fractions of the target and critical organs.

FIG. 13 is another example of prescription data for the human body model of FIG. 6. FIG. 14 is a graph illustrating another example of relationships between the scaling parameter and the second object function. FIG. 15 is a graph illustrating another example of relationships of the scaling parameter with the maximum value of the first and second indices and the maximum value of the third to fifth indices when determining the second object function. FIG. 16 is a graph illustrating another example of relationships between the normalized dose and the volume fractions of the target and critical organs. FIG. 17 is another example of underdose volume fraction of the target, the overdose volume fractions of the critical organs and so forth.

In FIG. 6, the reference numeral 80 designates a human body model, 82 designates a target, and 84, 86 and 88 each designate a critical organ. The human body model 80 is irradiated with three proton beams 90, 92 and 94 passing through ridge filters 96a, 96b and 96c for adjusting the dose levels in the depth direction, and through collimators 98a, 98b and 98c for adjusting the lateral dose distributions. Proton beam sources are not shown in this figure.

FIG. 8 is an isocontour plot of the dose distribution when irradiating the proton beams with irradiation doses calculated from the prescription data as shown in FIG. 7. In the prescription data as shown in FIG. 7, the minimum dose, prescription dose, maximum dose and underdose volume fraction for the target 82 are set at 58 grays (Gy), 60 Gy, 62 Gy and 5%, respectively; the limiting dose, maximum dose and overdose volume fraction for the critical organ 84 are set at 25 Gy, 20 Gy, and 10%, respectively; the limiting dose, maximum dose and overdose volume fraction for the critical organ 86 are set at 15 Gy, 10 Gy, and 10%, respectively; the limiting dose, maximum dose and overdose volume fraction for the critical organ 88 are set at 15 Gy, 10 Gy, and 10%, respectively; all the constrained weights are set at one; and the reference coordinates are placed at the center of the target 82. Such prescription data are defined in the international standard DICOM-RT. Items other than the foregoing items can also be added to the prescription data. When adding new items, the above-mentioned indices are calculated using the new items.

The second object function calculating section 16 and scaling parameter optimization section 17 calculate for various values of the scaling parameter the second object function for the critical organs and target as illustrated in FIG. 9. FIG. 10 illustrates the maximum value of the third to fifth indices for the target, and the maximum value of the first and second indices for the critical organs, when calculating the second object function. Accordingly, FIG. 9 shows the greater one of the maximum value of the third to fifth indices for the target and the maximum value of the first and second indices for the critical organs.

As illustrated in FIG. 9, the second object function takes a minimum value when the scaling parameter is one. Thus, the scaling parameter is determined at one, and is supplied to the irradiation dose determining section 18.

FIG. 11 illustrates the relationships between the normalized doses of the target 82 and critical organs 84, 86 and 88 and the fraction of the volume exposed to the irradiation dose above the normalized doses. For example, as for the critical organ 84, the volume fraction exposed to the normalized dose (20 Gy dose) of 0.33 or more is 0.92.

FIG. 12 shows the minimum dose, prescription dose, maximum dose and underdose volume fraction of the target 82, and the maximum values of the doses and overdose volume fractions of the critical organs 84, 86 and 88, which are obtained from the calculated irradiation doses from the portals. In this case, the irradiation dose ratios of the proton beams 90, 92 and 94 were 2:1:1.

Comparing the prescription data of FIGS. 7 and 12, it is seen that although the minimum dose and maximum dose of the target, and the limiting doses of the critical organs satisfy the prescription data, the underdose volume fraction of the target and the overdose volume fraction of the critical organs do not satisfy the prescription data. When the irradiation based the calculated irradiation doses does not satisfy the prescription data, the prescription data are changed as shown in FIG. 13, for example. Although the irradiation directions and the number of portals are also changed in general, an example as shown in FIG. 13 is handled here for simplicity.

In the prescription data as shown in FIG. 13, the minimum dose, prescription dose, maximum dose and underdose volume fraction for the target 82 are set at 58 Gy, 60 Gy, 62 Gy and 5%, respectively; the limiting dose, maximum dose and overdose volume fraction for the critical organ 84 are set at 25 Gy, 25 Gy, and 0%, respectively; the limiting dose, maximum dose and overdose volume fraction for the critical organ 86 are set at 17 Gy, 17 Gy, and 0%, respectively; the limiting dose, maximum dose and overdose volume fraction for the critical organ 88 are set at 9 Gy, 9 Gy, and 0%, respectively; all the constrained weights are set at one; and the reference coordinates are placed at the center of the target 82.

The second object function calculating section 16 and scaling parameter optimization section 17 calculate for various values of the scaling parameter the second object function for the critical organs and target as illustrated in FIG. 14. FIG. 15 illustrates the maximum value of the third to fifth indices for the target, and the maximum value of the first and second indices for the critical organs, when calculating the second object function. Accordingly, FIG. 14 shows the greater one of the maximum value of the third to fifth indices for the target and the maximum value of the first and second indices for the critical organs.

As illustrated in FIG. 14, the second object function takes a minimum value when the scaling parameter is 1.03. Thus, the scaling parameter is determined at 1.03, and is supplied to the irradiation dose determining section 18.

FIG. 16 illustrates the relationships between the normalized doses of the target 82 and critical organs 84, 86 and 88 and the fraction of the volume exposed to the irradiation dose above the normalized doses.

FIG. 17 shows the minimum dose, prescription dose, maximum dose and underdose volume fraction of the target 82, and the maximum values of the doses and overdose volume fractions of the critical organs 84, 86 and 88, which are calculated from the irradiated doses from the portals. In this case, the irradiation dose ratios of the proton beams 90, 92 and 94 were 1:0.8:0.4.

Comparing the prescription data of FIG. 13 with the data of FIG. 17, it is seen that the prescription data are satisfied for all the items. If the prescription data are not satisfied, they are further changed.

Although the broad beam irradiation of the proton beams using the ridge filters is described in the embodiment, the foregoing method of calculating the irradiation doses from the portals is also applicable, when forming a uniform dose distribution in the target for individual portals, to beam scanning irradiation of particle beams such as proton beams or carbon beams which scan small beam spots using scanning magnets or the like.

As described above, the present embodiment 1 calculates the foregoing indices from the prescription data about the doses prescribed by a physician for the target and critical organs; calculates from the prescription data the first and second object functions for the prescription data; and calculates the irradiation doses from the portals such that the object functions become minimum, that is, the prescription data are satisfied. This offers an advantage of being able to set appropriate irradiation doses in accordance with the prescription data.

The present embodiment of the irradiation dose calculating unit can be implemented by a computer including a recording medium that records a program for executing the foregoing processings.

EMBODIMENT 2

Although the embodiment 1 employs the iterative search method for optimizing the irradiation dose ratios when calculating the first object function, the present embodiment 2 employs a simulated annealing method or a gradient method like a conjugate gradient method instead of the iterative search method to optimize the irradiation dose ratios. It is also possible to begin the optimization with the simulated annealing method, and to change it to the conjugate gradient method in midstream of the optimization. The simulated annealing method and the gradient method like the conjugate gradient method are described in W. H. Press, et al., "Numerical Recipes in FORTRAN", second edition, Cambridge university press, 1992.

Thus, the present embodiment 2 optimizes the irradiation dose ratios using the simulated annealing method and the gradient method like the conjugate gradient method. This offers an advantage of being able to optimize the irradiation dose ratios efficiently.

EMBODIMENT 3

Although the embodiment 1 calculates the first and second object functions on the basis of the first to fifth indices, other indices are also available. Among them are indices multiplied by a penalty coefficient that increases when the dose uniformity or dose prescription condition in the target is not satisfied, and indices obtained by the volume integral of the doses for the critical organs. Furthermore, although the embodiment 1 adopts the maximum values of the indices as the first and second object functions, the total sum of the indices can be used as the first and second object functions.

According to the embodiment 3, an advantage like that of the embodiment 1 can be achieved by using other indices.

What is claimed is:

1. An irradiation dose calculating unit comprising:
   a prescription data input section for receiving prescription data including a prescription dose, a minimum dose, a maximum dose, and an underdose volume fraction for at least one target, and a limiting dose, a maximum dose, and an overdose volume fraction for at least one critical organ;
   an absorbed dose distribution calculating section for calculating absorbed dose distributions of radiation beams irradiated from a plurality of portals to the target;
   a first object function calculating section for calculating a first object function from the prescription data, irradiation dose ratios of the radiation beams irradiated from the portals to the target, and the absorbed dose distributions calculated by said absorbed dose distribution calculating section, the first object function indicating a level of satisfaction of the prescription data for the critical organ;
   an irradiation dose ratio calculating section for calculating the irradiation dose ratios that optimize the first object function;
   a second object function calculating section for calculating a second object function from the prescription data and a product of a scaling parameter multiplied by a sum of products obtained by multiplying the absorbed dose distributions for the portals by the irradiated dose ratios for the portals calculated by said irradiation dose ratio calculating section, the second object function indicating a level of satisfaction of the prescription data for the target and the critical organ;
   a scaling parameter calculating section for calculating the scaling parameter that optimizes the second object function; and
   an irradiation dose determining section for determining the irradiation doses from the portals from at least the scaling parameter calculated by said scaling parameter calculating section, the irradiation dose ratios for the portals calculated by said irradiation dose ratio calculating section, and the absorbed does distributions for the portals.

2. The irradiation dose calculating unit according to claim 1, wherein the absorbed dose distributions are normalized distributions obtained by dividing the absorbed dose distributions of the radiation beams irradiated from the portals to the target by an absorbed dose at reference coordinates in the target.

3. The irradiation dose calculating unit according to claim 1, wherein said first object function calculating section determines one of a first index and a second index as the first object function, the first index being calculated using a maximum value of the absorbed dose distributions in the critical organ, and the second index being calculated using a volume fraction of the critical organ, in which the absorbed dose is at least equal to a threshold absorbed dose.

4. The irradiation dose calculating unit according to claim 1, wherein said irradiation dose ratio calculating section determines the irradiation dose ratios for the portals by varying the irradiation dose ratios for the portals step-by-step from zero to one, by having said first object function calculating section calculate the first object function at each step, and by determining the irradiation dose ratios for the portals when the first object function is optimized.

5. The irradiation dose calculating unit according to claim 4, wherein said irradiation dose ratio calculating section determines the irradiation dose ratios only for portals with irradiation dose ratios less than unity.

6. The irradiation dose calculating unit according to claim 1, wherein said irradiation dose ratio calculating section calculates the irradiation dose ratios using an optimization method selected from a group consisting of an iterative search method, a simulated annealing method, a gradient method, and combinations of at least two of the iterative search method, the simulated annealing method, and the gradient method.

7. The irradiation dose calculating unit according to claim 1, wherein said second object function calculating section determines one of a first index, second index, third index, fourth index, and fifth index as the second object function, the first index being calculated using a maximum value in the critical organ of the product of the scaling parameter multiplied by the sum of products obtained by multiplying the absorbed dose distributions for the portals by the irradiated dose ratios for the portals calculated by said irradiation dose ratio calculating section, the second index being calculated using the overdose volume fraction of the critical organ in which the absorbed dose exceeds a threshold absorbed dose, the third index being calculated using a minimum value in the target of the product of the scaling parameter and the sum of the products, the fourth index being calculated using a maximum value in the target of the product of the scaling parameter and the sum of the products, and the fifth index being calculated using the volume fraction of the target in which the absorbed dose is less than the threshold absorbed dose.

8. The irradiation dose calculating unit according to claim 1, wherein said irradiation dose determining section places a product of the scaling parameter and the prescription dose for the target as an absorbed dose at the reference coordinates in the target, and determines the irradiation doses for the portals from the absorbed dose.

9. The irradiation dose calculating unit according to claim 8, wherein said irradiation dose determining section places the product of the scaling parameter and the prescription dose for the target as the absorbed dose of the reference coordinates in the target, obtains a proportionality constant by dividing the absorbed dose by the absorbed dose at the reference coordinates obtained from the sum of products of the absorbed dose ratios for the portals and absorbed doses for the portals per unit irradiation dose, and determines the irradiation doses of the portals by multiplying the irradiation dose ratios by the proportionality constant.

10. An irradiation dose calculating method comprising:

inputting prescription data including a prescription dose, a minimum dose, a maximum dose, and an underdose volume fraction for at least one target, and including a limiting dose, a maximum doses and an overdose volume fraction for at least one critical organ;

calculating absorbed dose distributions of radiation beams irradiated from a plurality of portals to the target;

calculating a first object function from the prescription data, irradiation dose ratios of the radiation beams irradiated from the portals to the target, and the absorbed dose distributions, the first object function indicating a level of satisfaction of the prescription data for the critical organ;

calculating the irradiation dose ratios that optimize the first object function;

calculating a second object function from the prescription data and a product of a scaling parameter multiplied by a sum of products obtained by multiplying the absorbed dose distributions for the portals by the irradiated dose ratios for the portals, the second object function indicating a level of satisfaction of the prescription data for the target and the critical organ;

calculating the scaling parameter that optimizes the second object function; and determining the irradiation doses for the portals from at least the scaling parameter calculated, the irradiation dose ratios for the portals calculated, and the absorbed does distribution for the portals.

11. A computer usable medium having a computer readable program code means for causing a computer to function as an irradiation dose calculating unit comprising:

a prescription data input section for receiving prescription data including a prescription dose, a minimum dose, a maximum dose, and an underdose volume fraction for at least one target, and a limiting dose, a maximum dose, and an overdose volume fraction for at least one critical organ;

an absorbed dose distribution calculating section for calculating absorbed dose distributions of radiation beams irradiated from a plurality of portals to the target;

a first object function calculating section for calculating a first object function from the prescription data, irradiation dose ratios of the radiation beams irradiated from the portals to the target, and the absorbed dose distributions calculated by said absorbed dose distribution calculating section, the first object function indicating a level of satisfaction of the prescription data for the critical organ;

an irradiation dose ratio calculating section for calculating the irradiation dose ratios that optimize the first object function;

a second object function calculating section for calculating a second object function from the prescription data and a product of a scaling parameter multiplied by a sum of products obtained by multiplying the absorbed dose distributions for the portals by the irradiated dose ratios for the portals calculated by said irradiation dose ratio calculating section, the second object function indicating a level of satisfaction of the prescription data for the target and the critical organ;

a scaling parameter calculating section for calculating the scaling parameter that optimizes the second object function; and an irradiation dose determining section for determining the irradiation doses from the portals from at least the scaling parameter calculated by said scaling parameter calculating section, the irradiation dose ratios for the portals calculated by said irradiation dose ratio calculating section, and the absorbed does distributions for the portals.

* * * * *